United States Patent [19]

Yoshimoto et al.

[11] Patent Number: 4,918,172
[45] Date of Patent: Apr. 17, 1990

[54] ANTHRACYCLINE ANTIBIOTICS

[75] Inventors: Akihiro Yoshimoto, Fujisawa; Osamu Jodo, Yokohama; Yoshio Watanabe; Rokuro Okamoto, both of Fujisawa; Tomoyuki Ishikura, Chigasaki; Hiroshi Naganawa, Tokyo; Tsutomu Sawa, Ayase; Tomio Takeuchi, Tokyo, all of Japan

[73] Assignee: Sanraku Incorporated, Tokyo, Japan

[21] Appl. No.: 252,636

[22] Filed: Oct. 3, 1988

[30] Foreign Application Priority Data

Oct. 6, 1987 [JP] Japan ................. 62-250712
Aug. 25, 1988 [JP] Japan ................. 63-211624

[51] Int. Cl.$^4$ .................. C07H 15/24; A61K 31/71
[52] U.S. Cl. ............................. 536/6.4; 536/16.8
[58] Field of Search ............. 536/6.4, 16.8; 425/78; 514/34

[56] References Cited

U.S. PATENT DOCUMENTS 4,316,011 2/1982 Oki et al. ..................... 536/17 A
4,439,603 3/1984 Umezawa et al. ............. 536/6.4

OTHER PUBLICATIONS

Yoshimoto et al. (1984) J. Antibiotic 37(8): 920–2 (Abstract CA 101: 192369a).
(Abstract CA 108: 93081p) JP Patent 62,138196, 6/87, Odakawa et al.
(Abstract CA 99: 122833p) European Pat. 78447, 5-83, Yoshimoto et al.

Primary Examiner—Johnnie R. Brown
Assistant Examiner—Gary Kunz
Attorney, Agent, or Firm—Jordan and Hamburg

[57] ABSTRACT

Disclosed are anthracycline antibiotics of a formula (I):

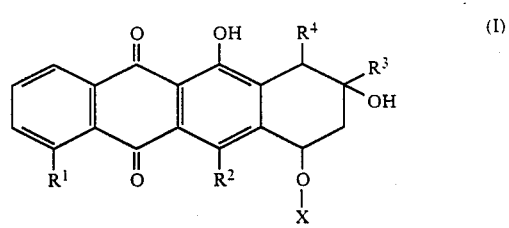

in which $R^1$ and $R^2$ are hydroxyl groups, $R^3$ is ethyl group, $R^4$ is methoxycarbonyl group and X represents daunosamine-rhodenose or daunosamine-deoxyfucose; or $R^1$ and $R^2$ are hydroxyl groups, $R^3$ is 1-hydroxyethyl group, $R^4$ is hydrogen atom and X represents daunosamine-rhodenose or daunosamine-deoxyfucose; or $R^1$, $R^2$ and $R^4$ are hydroxyl groups, $R^3$ is ethyl group and X represents daunosamine-rhodenose, daunosamine-deoxyfucose, rhodosamine-rhodenose, N-monomethyldaunosamine-rhodenose or N-monomethyldaunosamine-deoxyfucose; or $R^1$ is methoxy group, $R^2$ is hydroxyl group, $R^3$ is ethyl group, $R^4$ is methoxycarbonyl group and X represents daunosamine-rhodenose or daunosamine-deoxyfucose; or $R^1$ and $R^4$ are hydroxy groups, $R^2$ is hydrogen atom, $R^3$ is ethyl group and X represents daunosamine-deoxyfucose, as well as pharmaceutically acceptable acid addition salts thereof. The antibiotics (I) have a carcinostatic activity and are useful as a carcinostatic for murine leukemia L1210 cells in culture.

13 Claims, No Drawings

ANTHRACYCLINE ANTIBIOTICS

BACKGROUND OF THE INVENTION

1. Field of the Invention

The present invention relates to novel anthracycline antibiotics having a carcinostatic activity.

2. Prior Art

As carcinostatic anthracycline antibiotics, hitherto, daunomycin (refer to U.S. Pat. No. 3,616,242) and adriamycin (refer to U.S. Pat. No. 3,590,028) are known, and these two are compounds which are most widely utilized for clinical use at present as a carcinostatic chemotherapeutical agent. However, these have serious cardiotoxic activity and myelotoxic activity, even though they have an excellent carcinostatic activity. Therefore, these are not absolutely satisfactory as carcinostatic agents. Under the circumstances, production of compounds whose harmful side effect is reduced and whose carcinostatic activity is improved is desired, and some anthracycline antibiotics have already been proposed to be produced by means of a fermentation method, microbial conversion method and chemical synthesis method. For instance, specific examples of known antibiotics include acracinomycin A and acracinomycin B (refer to JP-B No. 51-34914 - the term "JP-B" as used herein means an "examined Japanese patent publication"), rhodomycin antibiotics (refer to JP-A No. 56-15299 - the term "JP-A" as used herein means an "unexamined published Japanese patent application"), 4'-O-tetrahycoropyranyl-adriamycin (refer to JP-B No. 57-13558), 3'-deamino-3'-morpholino-daynomycin and 3'-deamino-3'-morpholino-adriamycin (refer to JP-A No. 57-163393). Other daunomycin and adriamycin derivatives are described in Topics in Antibiotics Chemistry, Vol. 12, pages 102 to 279 (published by Ellis Horwood Limited) and The Chemistry of Antitumor Antibiotics, Vol. 1, pages 63 to 132 (published by Wiley-Interscience).

As a tumoricidal agent, various kinds of analogous compounds of anthracycline antibiotics have been proposed, as mentioned above, and some of them have already been widely utilized for clinical use while some others have been put to a clinical demonstration. However, none are satisfactory in both the non-toxicity and the carcinostatic activity. In addition, in most tumoricides, the in vivo test results and animal test results are not always related directly to the carcinostatic activity of human cancers, and therefore, many-sided studies are required for tumoricidal substances. Accordingly, regarding the anthracycline carcinostatics which have been evaluated to be effective to some degree as a tumoricide, there is a desire to obtain a new group of compounds which are more effective as a clinical medicine.

The present inventors have previously illustrated methods of producing specific new anthracycline antibiotics having an excellent activity by microbial conversion of various anthracycline-aglycones with an aclacinomycin-producing strain (Streptomyces galilaeus KE 303 (FERM BP-2048). For example, refer to JP-A No. 56-15299 (rhodomycin antibiotics) and JP-A No. 57-165399 (2-hydroxyacracinomycin A).

SUMMARY OF THE INVENTION

The object of the present invention is to provide anthracycline antibiotics which are new and have a strong tumoricidal activity.

Using various anthracyclines as a conversion substrate in microbial conversion, the present inventors produced new anthracycline antibiotics additionally having a neutral saccharide residue at the 4'-position and investigated the tumoricidal activity of the new antibiotics. As a result, we found substances having an extremely strong tumoricidal activity among the new antibiotics and have hereby achieved the present invention.

Accordingly, the subject matter of the present invention is to provide new anthracycline antibiotics of a formula (I):

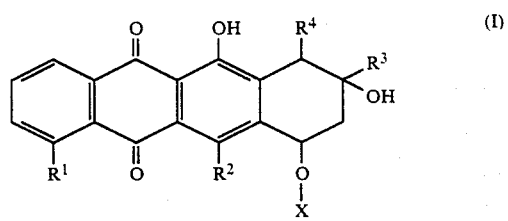

in which $R^1$ and $R^2$ are hydroxyl groups, $R^3$ is ethyl group, $R^4$ is methoxycarbonyl group and X represents daunosamine-rhodenose or daunosamine-deoxyfucose; or $R^1$ and $R^2$ are hydroxyl groups, $R^3$ is 1-hydroxyethyl group, $R^4$ is hydrogen atom and X represents daunosamine-rhodenose or daunosamine-deoxyfucose; or $R^1$, $R^2$ and $R^4$ are hydroxyl groups, $R^3$ is ethyl group and X represents daunosamine-rhodenose, daunosamine-deoxyfucose, rhodosamine-rhodenose, N-monomethyldaunosamine-rhodenose or N-monomethyldaunosamine-deocyfucose; or $R^1$ is methoxy group, $R^2$ is hydroxyl group, $R^3$ is ethyl group, $R^4$ is methoxycarbonyl group and X represents daunosamine-rhodenose or daunosamine-deoxyfucose; or $R^1$ and $R^4$ are hydroxy groups, $R^2$ is hydrogen atom, $R^3$ is ethyl group and X represents daunosamine-deoxyfucose, as well as pharmaceutically acceptable addition salts thereof.

DETAILED DESCRIPTION OF THE INVENTION

The new anthracycline antibiotics of the present invention include the following compounds:

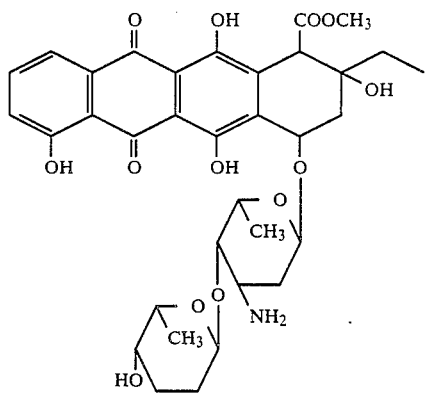
(This is called CG17A.)     (I-a)
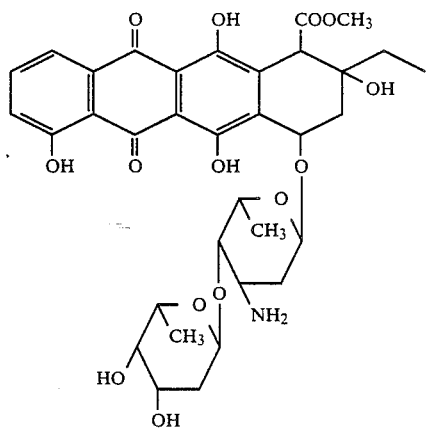
(This is called CG17B.)     (I-b)
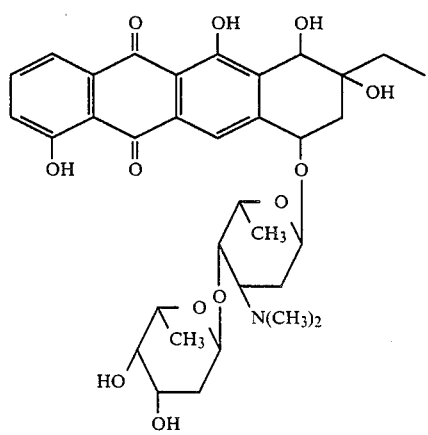
(This is called CG18B.)     (I-c)
-continued
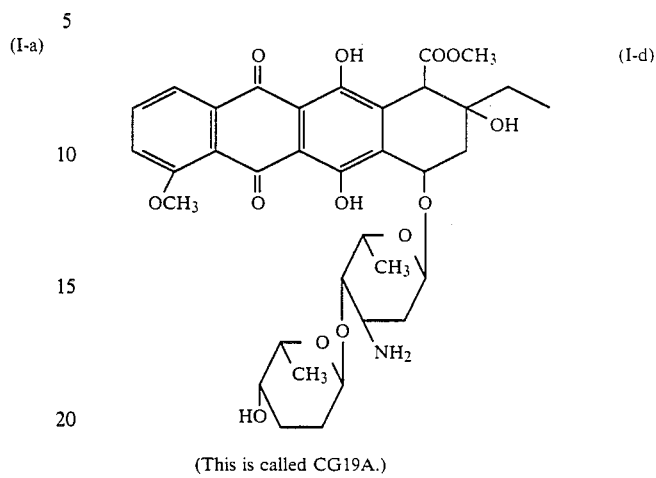
(This is called CG19A.)     (I-d)
(This is called CG19B.)     (I-e)
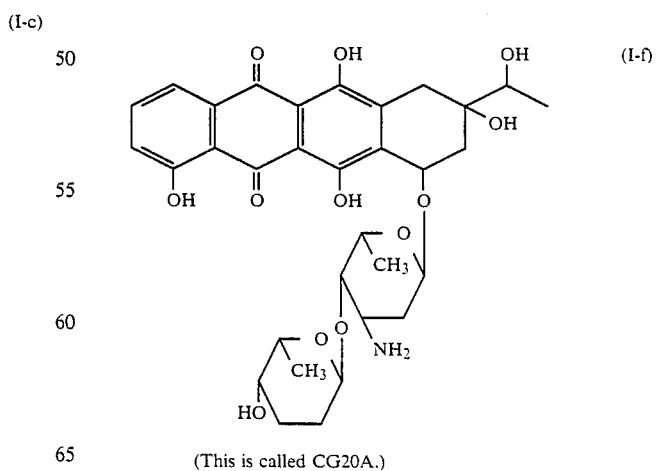
(This is called CG20A.)     (I-f)

-continued

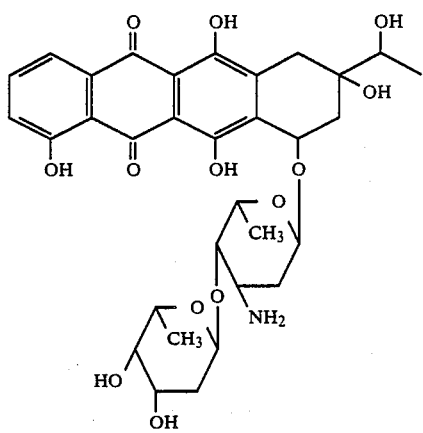

(This is called CG20B.)

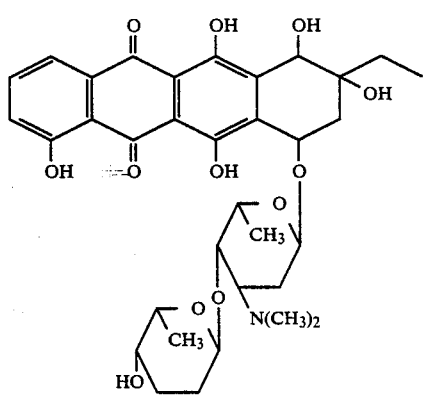

(This is called CG21A.)

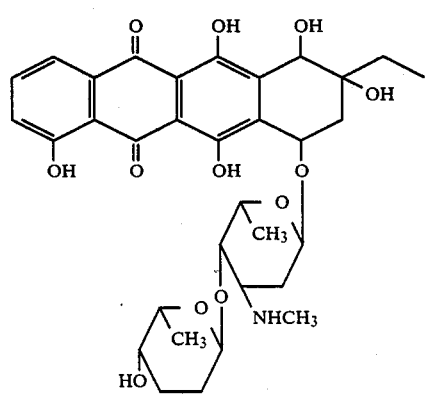

(This is called CG22A.)

-continued

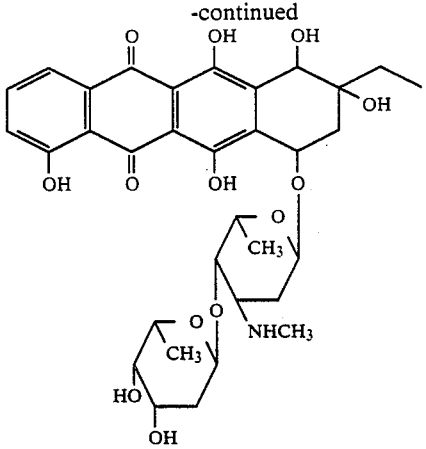

(This is called CG22B.)

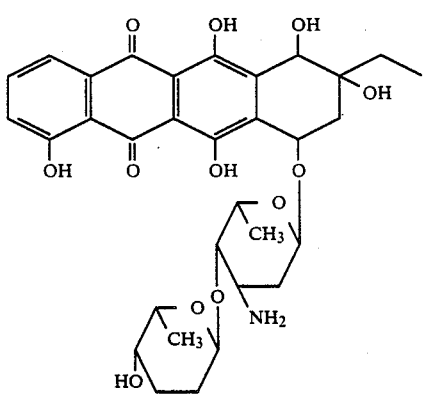

(This is called CG15A.)

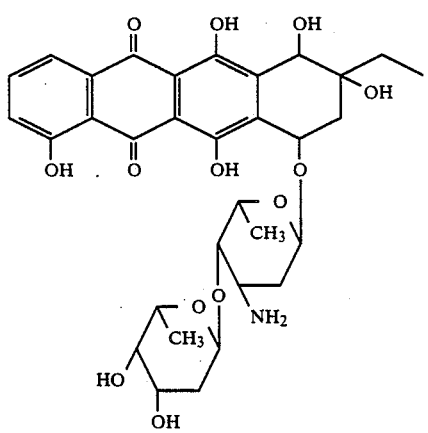

(This is called CG15B.)

These antibiotics are useful not only as a tumoricidal substance by themselves but also as a nucleus for producing chemical derivatives in the form having a saccharide chain or a low molecular or high molecular active substance as bonded to the nucleus.

The anthracycline antibiotics of the present invention are produced from the following compounds as a starting material. The starting materials for producing the anthracycline antibiotics of the present invention are compounds as represented by the following formula (II):

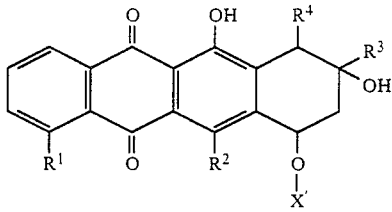 (II)

in which R¹ and R² are hydroxy groups, R³ is ethyl group, R⁴ is methoxycarbonyl group and X' is daunosamine (D788-6);

R¹ and R⁴ are hydroxyl groups, R² is hydrogen atom, R³ is ethyl group and X' is daunosamine (Y262-3); R¹ is methoxy group, R² is hydroxyl group, R³ is ethyl group, R⁴ is methoxycarbonyl group and X' is daunosamine (D788-5);

R¹ and R² are hydroxyl groups, R³ is 1-hydroxyethyl group, R⁴ is hydrogen atom and X' is daunosamine (dihydrocarminomycin);

R¹, R² and R⁴ are hydroxyl groups, R³ is ethyl group and X' is daunosamine (D788-7);

R¹, R² and R⁴ are hydroxyl groups, R³ is ethyl group and X' is rhodosamine (β-rhodomycin-1); or R¹, R² and R⁴ are hydroxyl groups, R³ is ethyl group and X' is N-monomethyldaunosamine (LB-1).

The anthracycline compounds of the present invention are produced by microbial treatment of the above-mentioned anthracycline compounds as a starting material.

As a strain of microorganisms to be used for production of the anthracycline compounds of the present invention, a mutant derived form a soil strain or a known strain, which belongs to Actinomycetes sp. and which has an ability of producing aclacinomycins, cinerbin or rhodomycins and analogues thereof, by mutagenetic treatment with a mutagen such as an ultraviolet ray or N-methyl-N'-nitro-N-nitrosoguanidine (NTG), may be used, the mutant having no ability for the production of antibiotics and dyes but having an ability of bonding one rhodenose or deoxyfucose to the anthracycline compound of the aforesaid formula (II) which is used as a starting compound at the 4'-OH position thereof. The strain may be incubated in a medium having pertinent nutrient sources and the starting compound may be added during incubation thereby to obtain the intended anthracycline antibiotic or the formula (I) of the present invention. As one typical mutant which may be used in the present invention, a mutant strain *Streptomyces galilaeus* MA144-M1, KE303 (FERM BP-2048) which has been derived from *Streptmyces galilaeus* MA144-M1 (ATCC 31133 or FERM P-2455) known as a strain of producing an anthracycline antibiotic acracinomycin A (refer to JP-B No. 51-34915) is preferably mentioned, the said mutant strain not being antibiotic-producible but having the above-mentioned microbial convertibility. In addition, other mutant strains as derived from strains which are known as a cinerbin or rhodomycin producing strain and which have the above-mentioned microbial convertibility may also be used in the present invention. Concrete explanation for the method of isolation of the KE303 strain is described in JP-A No. 56-15299, which is referred to in place of explaining the method herein.

The anthracycline compounds of the aforesaid formula (II) which are used to be microbially converted in accordance with the present invention were isolated by the present inventors, which may be prepared in accordance with the method mentioned below.

Precisely, D788-6, D788-7 and dihydrocarminomycin may be prepared by incubating Streptomyces sp. D788, RPM-5 (FERM BP-811) which has been proposed to be a strain of producing anthracycline antibiotics D788-6, D788-7 and others, by the method described in JP-A No. 61-33194.

Y262-3 and β-rhodomycin-1 may be prepared by incubating Streptomyces violaceus A262, SC-7 (FERM BP-1331) which has been proposed to be a strain of producing Y262-1 and Y262-3, by the method described in Japanese Patent Application No. 61-210607.

On the other hand, D788-5 may be prepared by incubating Streptomyces sp. D788 4L-660 (FERN BP-2049), which has been proposed to be a strain of producing D788-5, by the method described in Japanese Patent Application No. 60-185797.

The methods for preparation of the anthracycline compounds will be mentioned concretely hereunder.

Preparation of Y262-3 and β-rhodomycin-1:

From a YS slant culture (0.3% yeast extract, 1% soluble starch, 1.5% agar, pH 7.2) of Streptomyces violaceus A262 SC7 (FERM BP-1331), a loopful of the microbial cells was taken out. This was inoculated in 100 ml of a sterilized seed culture medium (comprising the components mentioned below) which was put in a 500 ml Erlenmeyer flask and then cultivated on a rotary shaker (200 rpm) at 28° C. for 3 days with shaking to prepare a seed culture.

| Seed Culture Medium: | |
|---|---|
| Soluble Starch | 0.5% |
| Glucose | 0.5 |
| Essan Meat | 1.0 |
| (soybean powder, manufactured by Ajinomoto Co.) | |
| Yeast Extract | 0.1 |
| Sodium Chloride | 0.1 |
| Potassium Secondary Phosphate | 0.1 |
| Magnesium Sulfate (7H₂O) | 0.1 |
| Tap water | |
| pH 7.4 (before sterilized) | |

Next, 15 liters of a production medium comprising the components mentioned below was put in a 30 liter jar fermenter and sterilized, and 750 ml (which corresponds to 5%) of the above-mentioned seed culture was added and inoculated thereto.

| Production Medium: | |
|---|---|
| Soluble Starch | 4.0%, pH 8.2 |
| (before sterilized) | |
| Essan Meat | 2.5 |
| Yeast Extract | 0.1 |
| Sodium Chloride | 0.25 |
| Calcium Carbonate | 0.3 |
| Mineral Mixture* | 0.2 |
| Tap water to make | 15 liters |

*2.8 g of CuSO₄4%H₂O, 0.4 g of FeSO₄7H₂O, 3.2 g of MnSO₄4H₂O and 0.8 g of ZnSO₄2H₂O were dissolved in 500 ml of distilled water.

The incubation was conducted under the condition of aeration of 15 liters/min, stirring at 300 rpm and temperature of 28° C. for 130 hours. The culture liquid was collected and adjusted to have pH of 1.0 with 6N hydrochloric acid and then gently heated at 65° C. for 2 hours. Then a filtration aid was added thereto in amount of 2% and the liquid was filtered. 10 liters of acetone was added to the fraction of mycelial cake and extracted the same for one hour and then filtered to obtain an acetone extract. This was concentrated under reduced pressure to about 2 liters, adjusted to have pH of 8.0 with 4N sodium hydroxide and then extracted with chloroform (4 liters in total). On the other hand, the supernatant fraction was adjusted to have pH of 8.0 with 4N sodium hydroxide and then extracted with 3 liters of chloroform. Both chloroform extract layers obtained were combined and washed with an aqueous saturated solution of sodium chloride. Then this was dried over anhydrous sodium sulfate. The chloroform extract layer was taken out by filtration and concentrated under reduced pressure to a small amount. An excess amount of n-hexane was added thereto to form a precipitate, which was then collected by filtration. This was dried in vacuum to obtain 10.9 g of a crude powder containing β-rhodomycin-1 and Y262-3.

10.9 g of the crude powder was dissolved in chloroform and absorbed to 105 g of silicagel column (column diameter 35 mm: Wako-gel C-100 manufactured by Wako Pure Chemical Co.) previously filled with chloroform. This was first developed with a mixed developer of chloroform/methanol (100/1) to remove impurities containing aglycones and then developed with a mixed developer of chloroform/methanol (10/1) to elute β-rhodomycin-1 and Y262-3. The eluate thus obtained was concentrated to dryness under reduced pressure to obtain a single composition product of β-rhodomycin-1 and a partially pure product of Y262-3.

Regarding the partially purified product of Y262-3, this was further purified with a fractionating thin silicagel layer (20×20 cm: PF$_{254}$ Silicagel manufactured by Merck Co.). Briefly, a solution of the partially pure product as dissolved in a mixed solvent of chloroform/methanol (15/1) was crosswise applied to the thin layer plate at the position 15 mm above the bottom end thereof, dried with air and then developed with a mixed solvent of chloroform/methanol/formic acid (4/1/0.1). The Y262-3-containing fraction was collected and extracted with a mixed solvent of chloroform/methanol (7/1). A necessary amount of water was added to the resulting extract, the aqueous layer was adjusted to a pH of 8.0 with 4N sodium hydroxide and shaken. The lower layer separated was isolated and concentrated to dryness under reduced pressure to obtain a single composition product of Y262-3.

Next, each product thus obtained was dissolved in a necessary amount of 0.1M acetic acid buffer (pH 3.0) and extracted twice with a ½ time amount of toluene. The aqueous layer was adjusted to a pH of 7.5 with an aqueous saturated solution of sodium bicarbonate and extracted with chloroform. The resulting chloroform extracted was washed with water and dried over anhydrous sodium sulfate. Then this was filtered and concentrated under reduced pressure to a small amount. An excess amount of hexane was added thereto to form a precipitate. The precipitate was collected by filtration and dried in vacuum to obtain a powder having a purity of 95% or more of β-rhodomycin-1 or Y262-3. The yield of β-rhodomycin-1 powder was 5200 mg and that of Y262-3 powder was 110 mg.

Preparation of D788-6 and dihydrocarminomycin:

From a YS slant culture (0.3% yeast extract, 1% soluble starch, 1.5% agar, pH 7.2) of Streptomyces sp. D788, RPM-5 (FERM BP-811) a loopful of the microbial cells was taken out. This was inoculated in 100 ml of a sterilized seed culture medium comprising the components mentioned below, which was put in a 500 ml Erlenmeyer flask and then cultivated on a rotary shaker (230 rpm) at 28° C. for 2 days with shaking to prepare a seed culture.

| Seed Culture Medium: | |
|---|---|
| Soluble Starch | 0.5% |
| glucose | 0.5 |
| Essan Meat | 1.0 |
| Yeast Extract | 0.1 |
| Sodium Chloride | 0.1 |
| Potassium Secondary Phosphate | 0.1 |
| Magnesium Sulfate (7H$_2$O) | 0.1 |
| Tap water | |
| pH 7.4 (before sterilized) | |

Next, 15 liters of a production medium comprising the components mentioned below was put in a 30 liter jar fermenter and sterilized, and 150 ml (which corresponds to 15%) of the above-mentioned seed culture was added and inoculated thereto.

| Production Medium: | |
|---|---|
| Taiwan Yeast | 5% |
| Soluble Starch | 7.5 |
| Yeast Extract | 0.2 |
| Sodium Chloride | 0.2 |
| Calcium Carbonate | 0.3 |
| Mineral Mixture* | 0.06 |
| Tap water | |
| pH 8.2 (before sterilized) | |

*A small amount of hydrochloric acid was added to 2.8 g of CuSO$_4$5H$_2$O, 0.4 g of FeSO$_4$7H$_2$O, 3.2 g of MnCl$_2$4H$_2$O and 0.8 g of ZnSO$_4$2H$_2$O and dissolved in 500 ml of distilled water.

The incubation was conducted under the condition of aeration of 15 liters/min, stirring at 350 rpm and temperature of 28° C. for 130 hours, whereby the culture liquid became dark violet because of the product formed therein. The culture broth was taken out from the jar fermenter, diluted with water to ½ concentration, adjusted to a pH of 1.3 with concentrated sulfuric acid and then stirred for about one hour at room temperature. A filtration aid was added thereto in an amount of 2% and the mycelial cells were separated by filtration to isolate 29.5 liters of filtrate. The mycelial cake was suspended in 6 liters of acetone and stirred for 20 minutes for extraction. After filtration, the acetone extract was taken out and concentrated under reduced pressure to about 1.5 liters. This was combined with the previous filtrate.

The thus combined filtrate was passed through a column (pH 1.5) containing 1000 ml of Diaion HP-20 (synthetic absorbent resin, manufactured by Mitsubishi Kasei Corp.) at SV of 4.5 so that the product was absorbed into the resin. The column was washed with 2000 ml of an aqueous dilute sulfuric acid (pH 1.5) and then the absorbed product was eluted with 1500 ml of 50% acetone (pH 1.7). The eluate was concentrated under reduced pressure to about 600 ml and then this was adjusted to a pH of 8.5 with 4N sodium hydroxide and extracted with chloroform (3000 ml in total). The chloroform extract thus obtained was washed with an aqueous 20% sodium chloride solution and dried with anhydrous sodium sulfate. After filtration, the resulting filtrate was concentrated under reduced pressure to a small amount, and an excess amount of n-hexane was added thereto to form a precipitate. The precipitate was collected by filtration and dried in vacuum to obtain 2.48 g of a crude powder containing D788-6 and dihydrocarminomycin.

100 g of Wako Silicagel C-200 (manufactured by Wako Pure Chemical Co.) was filled in a column with a mixed solvent of chloroform/methanol (20/1), and a solution of the total amount of the above-obtained crude powder dissolved in a mixed solvent of chloroform/methanol (20/1) was absorbed to the upper layer of the silicagel column, which was then developed with the same solvent system. The first eluted aglycones were removed and the column content was then developed with 600 ml of a mixed solvent of chloroform/methanol (15/1), 500 ml of a mixed solvent of chloroform/methanol (13/1) and 550 ml of a mixed solvent of chloroform/methanol (12/1) in this order, thereby to elute a fraction of D788-6. Next, the column content was further developed with 500 ml of a mixed solvent of chloroform/methanol (10/1), 600 ml of a mixed solvent of chloroform/methanol/water (200/20/0.5) and 600 ml of a mixed solvent of chloroform/methanol/water (180/20/1) in this order, thereby to elute a fraction containing dihydrocarminomycin.

Each fraction was concentrated to dryness to obtain 130 mg or 145 mg of a partially pure powder. This was further purified with a fractionating thin silicagel layer (20×20 cm: $PF_{254}$ Silicagel, manufactured by Merck Co.) as mentioned below.

Briefly, the above-mentioned D788-6-containing powder was dissolved in a mixed solvent of chloroform/methanol (20/1) and crosswise spotted to the thin layer plate at the position 15 mm above the bottom thereof and then developed with a mixed solvent of chloroform/methanol/water (25/10/1). The D788-6 band was collected and extracted with a mixed solvent of chloroform/methanol (8/1). After being concentrated to dryness, this was dissolved in 0.1M acetic acid buffer (pH 3.0) and washed with chloroform. The aqueous layer remaining after extraction was adjusted to a pH of 8.5 with 4N sodium hydroxide and then extracted with chloroform. The resulting extract was washed with an aqueous 20% sodium chloride solution and then dried with anhydrous sodium sulfate. This was filtered and concentrated, and an excess amount of n-hexane was added thereto to form a precipitate. The precipitate was taken out by filtration and dried in vacuum to finally obtain 58 mg of a pure D788-6.

The other dihydrocarminomycin-containing fraction was also processed in the same manner as the purification of the D788-6 fraction, except that a mixed solvent of chloroform/methanol/water/acetic acid/concentrated aqueous ammonia (120/50/5/1/1) was used as a developing solvent and purification was conducted by thin layer chromatography and acid back dissolution, whereby 85 mg of a pure dihydrocarminomycin was obtained.

Preparation of D788-5:

From a YS slant culture (0.3% yeast extract, 1% soluble starch, 1.5% agar, pH 7.2) of Streptomyces D788, 4L-660 (FERM BP-2049) a loopful of the microbial cells was taken out. This was inoculated in 100 ml of a sterilized seed culture medium (comprising the components mentioned below) which was put in a 500 ml Erlenmeyer flask and then cultivated on a rotary shaker (220 rpm) at 28° C. for 2 days with shaking to prepare a seed culture.

| Seed Culture Medium | |
| --- | --- |
| Soluble Starch | 0.5% |
| Glucose | 0.5 |
| Essan Meat | 1.0 |
| Yeast Extract | 0.1 |
| Sodium Chloride | 0.1 |
| Potassium Secondary Phosphate | 0.1 |
| Magnesium Sulfate ($7H_2O$) | 0.1 |
| Tap water | |
| pH 7.4 (before sterilized) | |

Next, 15 liters of a production medium comprising the components mentioned below was put in a 30 liter jar fermenter and sterilized, and 750 ml (which corresponds to 5%) of the above-mentioned seed culture was added and inoculated thereto.

| Production Medium: | |
| --- | --- |
| Taiwan Yeast | 5% |
| Soluble Starch | 7.5 |
| Yeast Extract | 0.3 |
| Sodium Chloride | 0.2 |
| Calcium Carbonate | 0.3 |
| Mineral Mixture* | 0.06 |
| Tap water | |
| pH 8.2 (before sterilized) | |

*2.8 g of $CuSO_4 5H_2O$, 0.4 g of $FeSO_4 7H_2O$, 3.2 g of $MnCl_2 4H_2O$ and 0.8 g of $ZnSO_4 7H_2O$ were dissolved in distilled water.

The incubation was conducted under the condition of aeration of 5 liters/min, stirring at 450 rpm and temperature of 28° C. for 130 hours, whereby the culture liquid became dark reddish brown and this contained about 300 μg.ml of D788-5.

30 liters of acetone was added to about 14 liters of the thus obtained culture liquid. The resulting mixture was adjusted to a pH of 3.5 with stirring and then continuously stirred further for 1 hour. This was filtered under suction by the use of a filtration aid (topco perlite), and the resulting filtrate thus obtained was concentrated under reduced pressure to 10 liters. The concentrated liquid was extracted two times each with 10 liters of chloroform at pH of 7.5. The thus obtained chloroform extract was back-dissolved in an acidic water (10 liters×2) at pH of 2.0. The resulting aqueous layer was adjusted to a pH of 7.5 with 4N sodium hydroxide and then extracted twice each with 5 liters of chloroform. The chloroform extract layer was dried with anhydrous sodium sulfate and then concentrated to dryness under reduced pressure to obtain 3.2 g of a crude powder of D788-5.

2.5 g of the crude D788-5 powder was dissolved in a small amount of chloroform and subjected to chromatography using a column (bed capacity: 300 ml) previously filled with silicagel (Wako Gel C-200, manufactured by Wako Pure Chemical Co.). As the substance was eluted with a mixed solvent of chloroform.methanol (10/1), the chromatography was observed by the above-mentioned TLC. The selected fraction was collected and concentrated under reduced pressure to a small amount. Five times by volume of n-hexane was added thereto to obtain 1.78 g of a pure D788-5.

Preparation of LB-1:

300 mg of β-rhodomycin-1 was dissolved in 200 ml of a mixed solvent of chloroform/methanol (100/1) and the resulting solution was irradiated in a light-irradiation device (UVL-400H-300P Type high pressure mercury lamp, manufactured by Rikoh Kagaku Sangyo KK), for 1 hour at 24° C. The reaction solution was concentrated to dryness under reduced pressure and then purified with a fractionating thin silicagel layer (20×20 cm: PF$_{254}$ Silicagel manufactured by Merck Co.). A solution of the reaction product a dissolved in a small amount of a mixed solvent of chloroform/methanol (15/1) was crosswise applied to the thin layer plate at a position 15 mm above the bottom end thereof, dried with air and then developed with a mixed solvent of chloroform/methanol/water/acetic acid (35/10/0.4/0.2). The silicagel layer fraction corresponding to LB-1 was collected and extracted with a mixed solvent of chloroform/methanol (6/1). Water was supplemented to the resulting extract and shaken, and the aqueous layer was adjusted to a pH of 8.0 with 4N sodium hydroxide. This was again well shaken so that the product was completely back-dissolved in the solvent layer. The solvent layer was concentrated to dryness under reduced pressure, and 20 ml of 0.1M acetic acid buffer (pH 3.5) was added thereto and dissolved. The resulting solution was washed by shaking twice with 10 ml of toluene. The aqueous layer was adjusted to a pH of 7.5 with an aqueous saturated solution of sodium bicarbonate and then extracted with chloroform. The resulting chloroform extract was washed with an aqueous saturated solution of sodium chloride, dried with anhydrous sodium sulfate and then concentrated under reduced pressure to a small amount. An excess amount of N-hexene was added thereto to form a precipitate. The precipitate was collected by filtration and dried in vacuum to obtain 82 mg of a pure LB-1 powder.

The compounds of the formula (I) of the present invention can be prepared as mentioned below.

Precisely, a strain having the above-mentioned microbial convertibility, which was cultivated on a YS agar slant medium and has been stored at 6° to 7° C., for example KE303 mutant strain, is inoculated in a medium comprising starch, glycerin, glucose or maltose as a carbon source, organic nitrogen-containing substances such as soybean powder, meat extract, yeast extract, peptone, corn steep liquor, cotton seed lees or fich powder as well as inorganic nitrogen containing nitrate or ammonium phosphate as a nitrogen source and inorganic salts and incubated therein at 25° to 35° C., preferably 28° C., for 15 to 48 hours, preferably 24 hours, with shaking or stirring. Then a methanol solution containing an anthracycline compound to be converted is added to the culture medium in a final concentration of from 10 to 500 µg/ml, preferably 50 µg/ml, and the medium is still incubated further for 15 to 96 hours, preferably 72 hours, with shaking to complete the microbial conversion of the anthracycline compound added. In order to prevent the medium from foaming during fermentation, Adekanol (manufactured by Asahi Denka Kogyo KK) or silicone (manufactured by Shinetsu Chemical Co.) may optionally be added as a defoaming agent.

In order to isolate the compound of the present invention from the culture broth, the culture broth is separated into mycelial cells and filtrate, and a crude dye containing the compound is extracted from the mycelial cake and the filtrate and then purified. For extraction may be used acetone, methanol, chloroform, ethyl acetate, toluene, dilute mineral acids or acid buffers. For purification, a column or thin layer chromatography using silicagel, crosslinked dextran gel (for example, Saphadex LH-20, manufactured by Pharmacia Co.) or a weak acidic ion-exchange resin, a liquid chromatography using a pertinent solvent or a countercurrent partition may advantageously be combined.

As the compound of the present invention has a basic amino-saccharide, this may be obtained in the form of a free base or also in the form of an addition salt with an inorganic acid or organic acid. The free base may be recovered in the form of an addition salt with a non-toxic salt, such as sulfuric acid, hydrochloric acid, nitric acid, malic acid, acetic acid, propionic acid, maleic acid, citric acid, succeinic acid, tartaric acid, fumaric acid, glutamic acid, pantoithenic acid, laurylsulfonyl acid or methanesulfonic acid, by a known method.

For formation of the addition salt, the free base may be reacted with the above-mentioned non-toxic acid in a pertinent solvent and then freeze-dried or the resulting addition salt may be precipitated in a solvent which hardly dissolves the salt.

The compound of the present invention thus obtained has been ascertained to be useful as a tumoricidal substance because of the results of the tumoricidal experiment against mouse leukemia L1210 culture cells mentioned below.

Activity of inhibition propagation of mouse leukemia L1210 culture cells and of inhibition synthesis of nucleic acid in the cells:

L1210 cells ($5 \times 10^4$/ml) were inoculated in RPMI 1640 medium (Rose Wellberg Laboratory) containing 20% calf serum, and the compound of the present invention (as indicated in Table 1 below) was added thereto in a concentration of from 0.0005 to 50.0 µg/ml. Thus the cells were incubated in a CO$_2$ incubator at 37° C. for 48 hours, and the 50% growth inhibiting concentration relative to the control group was obtained. The compound of the present invention was dissolved in M/50 acetic acid (pH 3.0) in a concentration of 1 µg/ml and then diluted with Dulbecco PBS (-) (manufactured by Nissui Pharmaceutical Co.), before being added to the medium.

On the other hand, the L1210 culture cells were suspended in a 10% calf serum-containing RPMI 1640 medium in a concentration of $8 \times 10^5$ cells/ml and then incubated in a CO$_2$ incubator at 37° C. for 1.5 hours. Then a solution of the compound of the present invention prepared as mentioned above was added to the medium in a different concentration. 15 minutes after the addition, $^{14}$C-uridine (0.05 µCi/ml) or $^{14}$C-thymidine (0.05 µCi/ml) was added and the medium was further incubated at 37° C. for an additional 60 minutes. A cold 10% trichloroacetic acid (TCA) was added to the reaction solution so that the reaction was stopped and the acid-insoluble substance was precipitated. This was washed twice with a cold 5% TCA and then dissolved in formic acid. Then the radioactivity of the resulting solution was measured, and the 50% uptake inhibiting concentration was obtained from the radioactivity uptake ratio relative to the control group. The results obtained are shown in Table 1 below.

TABLE 1

| | 50% Inhibiting Concentration (IC50: µg/ml) | | |
|---|---|---|---|
| Compound | Cell Growth Inhibition | DNA Synthesis Inhibition | RNA Synthesis Inhibition |
| CG15A | 0.002 | 1.2 | 3.0 |
| CG15B | 0.04 | 4.6 | 2.5 |
| CG17A | 0.5 | 3.3 | 1.1 |
| CG17B | 1.4 | 10.0 | 2.3 |
| CG18B | 0.16 | 2.6 | 2.3 |

TABLE 1-continued

| Compound | 50% Inhibiting Concentration (IC50: μg/ml) | | |
| --- | --- | --- | --- |
|  | Cell Growth Inhibition | DNA Synthesis Inhibition | RNA Synthesis Inhibition |
| CG19A | 1.0 | 4.8 | 1.3 |
| CG19B | 2.4 | 10.0 | 10.0 |
| CG20A | 0.17 | 1.2 | 1.2 |
| CG20B | 1.5 | 10.0 | 5.0 |
| CG21A | 0.012 | 0.38 | 0.18 |
| CG22A | 0.01 | 0.87 | 1.4 |
| CG22B | 0.21 | 5.0 | 10.0 |

The following examples are intended to illustrate the present invention in more detail but not to limit it in any way.

EXAMPLE 1

From a YS slant culture (0.3% yeast extract, 1% soluble starch, 1.5% agar, pH 7.2) of *Streptomyces galilaeus* MA144-M1, KE303 (FERM BP-2048), a loopful of the microbial cells was taken out. This was inoculated in 100 ml of a sterilized seed culture medium (comprising the components mentioned below) which was put in a 500 ml Erlenmeyer flask and then cultivated on a rotary shaker (220 rpm) at 28° C. for 2 hours with shaking to prepare a seed culture.

| Seed Culture Medium: | (w/v %) |
| --- | --- |
| Soluble Starch | 0.5% |
| Glucose | 0.5 |
| Soybean powder (Essan Meat) | 1.0 |
| Sodium Chloride | 0.1 |
| Potassium Secondary Phosphate | 0.1 |
| Magnesium Sulfate (7H$_2$O) | 0.1 |
| Tap water |  |
| pH 7.4 (before sterilized) |  |

Next, 5 liters of a production medium comprising the components mentioned below was put in each of three 10 liter jar fermenters and sterilized. Then 200 ml of the above-mentioned seed culture was added and inoculated to the production medium.

| Production Medium: | (w/v %) |
| --- | --- |
| Soluble Starch | 2.0% |
| Glucose | 1.0 |
| Soybean powder | 3.0 |
| Sodium Chloride | 0.3 |
| Potassium Secondary Phosphate | 0.1 |
| Magnesium Sulfate (7H$_2$O) | 0.1 |
| Yeast Extract | 0.1 |
| Mineral Mixture* | 0.1 (v/v %) |
| Defoaming Agent (Adekanol LG109) | 0.05 (v/v %) |
| Tap water |  |
| pH 7.0 (before sterilized) |  |

*2.8 g of CuSO$_4$·5H$_2$O, 0.4 g of FeSO$_4$, 3.2 g of MnCl$_2$·4H$_2$O and 0.8 g of ZnSO$_4$·2H$_2$O were dissolved in distilled water.

The incubation was conducted under the condition of aeration of 2.5 liters/min, stirring at 300 rpm and temperature of 28° C. for 1 day. A methanol solution of a substrate anthracycline compound (D788-6, Y262-3, β-rhodomycin-1, LB-1 or 13-dihydroicarminiomycin, 5 mg/ml) was added to the culture medium in an amount of 50 ml/jar (which corresponds to 250 mg of each substrate), and the incubation was continued for a further 3 days under the same condition.

The culture was recovered and subjected to centrifugation to separate the bacteria from the supernatant liquid. 10 liters of acetone was added to the bacteria and stirred and extracted, and the acetone extract was isolated by filtration. This was concentrated under reduced pressure to about 4 liters, adjusted to a pH of 3.0 with phospheric acid, extracted with 2 liters of chloroform and washed. Next, the resulting extract was adjusted to a pH of 8.0 with 4N sodium hydroxide and again extracted with 5 liters (total amount) of chloroform. The chloroform extract was concentrated under reduced pressure to a small amount, and an excess amount of n-hexane was added thereto to form a precipitate. The precipitate thus formed was collected by filtration and dried in vacuum to obtain a crude extract of a product converted from the respective substrat in an amount of from 270 to 460 mg.

EXAMPLE 2

275 g of the crude converted product powder obtained from the substrate D788-6 in Example 1 was subjected to silicagel column chromatography (diameter 30 mm, Silicagel C-200, manufactured by Wako Pure Chemical Co., 63 g) whereupon the column content was developed with the solvents mentioned below in order to elute a fraction mainly comprising CG17A and a fraction mainly comprising CG17B.

1. Chloroform/methanol (20/1); 20 ml
2. Chloroform/methanol/water (100/10/0.1); 200 ml
3. Chloroform/methanol/water (70/10/0.1); 180 ml Each of the both fractions was washed with water, concentrated to dryness and then purified by chromatography using a fractionating thin silicagel plate PF$_{254}$ (manufactured by Merck, 20×20 cm) and a solvent system of chloroform/methanol/water/acetic acid/concentrated aqueous ammonia (120/50/5/1/1). The red band separated, which corresponds to CG17A or CG17B, was collected, extracted with chloroform/methanol (5/1) and then washed with water. The solvent layer was concentrated to dryness.

This was dissolved in 20 ml of 1/50M acetic acid (pH 3.0) and extracted twice with 10 ml of solvent for washing. Then this was adjusted to a pH of 8.0 with 1N sodium hydroxide and extracted with 30 ml (total amount) of chloroform. The extract was washed with water, dried with anhydrous sodium sulfate and then concentrated. An excess amount of N-hexane was added thereto to form a precipitate, which was collected by filtration and dried in vacuum to obtain a pure CG17A powder or a pure CG17B powder. The yield of the pure CG17A powder was 12 mg and that of the pure CG17B powder was 34 mg.

Physico-chemical Properties of CG17A m.p. : 152° to 155° C. (decomposition)

$[\alpha]^{23}_D$: +400° (C=0.02, chloroform)

Mass (SI-MS): m/e 672 (M+H)$^+$

Ultraviolet and Visible Range Absorption Spectrum: ($\lambda^{90\% \, methanol}_{max \, nm} E^{1\%}_{1 \, cm}$): 204 (289), 235 (630), 254 (380) 294 (130), 493 (218), 527sh (146).

IR Spectrum ($\nu^{KBr}_{MAX}$cm$^{-1}$): 3400, 2920, 1725, 1600, 1430, 1400, 1290, 1240, 1195, 1165, 1120, 1070, 1000.

H-NMR Spectrum (CDCl$_3$) (δppm): 1.11 (t, 3H), 1.17 (d, 3H), 1.26 (d, 3H) 2.2–2.4 (—, 2H), 3.0 (m, 1H), m 3.51 (b, 1H), 3.62 (b, 1H), 3.71 (s, 3H), 4.12 (—, 1H), 4.20 (—, 1H), 4.29 (s, 1H), 4.86 (b, 1H), 5.23 (b, 1H), 5.48 (b, 1H), 7.25 (d, 1H), 7.69 (t, 1H), 7.89 (d, 1H).

Physico-chemical Properties of CG17B m.p. : 197° to 202° C. (decomposition)

[α]$^{23}_D$: +67° (C=0.02, chloroform)

Mass (SI-MS): m/e 688 (M+H)+

Ultraviolet and Visible Range Absorption Spectrum: ($\lambda^{90\% \ methanol}_{max \ nm} E^{1\%}_{1 \ cm}$): 204 (273), 235 (600), 254 (355) 294 (120), 493 (213), 526sh (137).

IR Spectrum ($\nu^{KBr}_{MAX} cm^{-1}$): 3400, 2930, 1725, 1600, 1430, 1400, 1290, 1240, 1195, 1165, 1120, 1010, 990, 805.

$^1$H-NMR Spectrum (CDCl$_3$, δppm): 1.10 (t, 3H), 1.29 (d, 3H), 1.30 (d, 3H), 2.30 (b, 2H), 3.0 (m, 1H), 3.50 (b, 1H), 3.67 (b, 1H), 3.73 (s, 3H), 4.1 -(−, 1H), 4.2 (−, 2H), 4.30 (s, 1H), 4.95 (b, 1H), 5.22 (b, 1H), 5.47 (b, 1H), 7.27 (dd, 1H), 7.69 (t, 1H), 7.88 (dd, 1H).

EXAMPLE 3

321 mg of the crude converted extract obtained from the substrate B-rhodomycin-1 in Example 1 was subjected to silicagel column chromatography (diameter 30 mm, Silicagel C-200, manufactured by Wako Pure Chemical Co., 38 g), whereupon the column content was developed with the solvents mentioned below in order to elute a partially purified fraction mainly comprising CG21A and a partially purified fraction mainly comprising CG21B.

1. Chloroform/methanol (21/1); 75 ml
2. Chloroform/methanol/water (100/10/0.1); 150 ml
3. Chloroform/methanol/water (70/10/0.1); 120 ml Then the fractions were processed in the same manner as in Example 2 for purification by thin layer chromatography and acid back-dissolution. Thus 6 mg of a powder of CG21A and 16 mg of a powder of CG21B were obtained.

Physico-chemical Properties of CG21A m.p. : 158° to 162° C. (decomposition)

[α]$^{23}_D$: −10° (C=0.02, chloroform)

Mass (SI-MS): m/e 658 (M+H)+

Ultraviolet and Visible Range Absorption Spectrum: ($\lambda^{90\% \ methanol}_{max \ nm} E^{1\%}_{1 \ cm}$): 204 (281), 235 (607), 254 (352) 293 (116), 495 (221), 529 (148).

IR Spectrum ($\nu^{KBr}_{MAX} cm^{-1}$): 3400, 2930, 1600, 1435, 1405, 1295, 1240, 1195, 1165, 1070, 1005, 810, 775, 715.

$^1$H-NMR Spectrum (CDCl$_3$, δppm): 1.15 (t, 3H), 1.23 (d, 3H), 1.29 (d, 3H), 2.19 (s, 6H), 2.2 (−, 2H), 3.60- (b, 1H), 3.81 (b, 1H), 4.0-4.3 (−, 2H), 4.94 (s, 1H), 4.94 (b, 1H), 5.16 (b, 1H), 5.54 (b, 1H), 7.34 (d, 1H), 7.74 (t, 1H), 7.93 (d,n 1H).

Physico-chemical Properties of CG21B m.p. : 165° to 168° C. (decomposition)

[α]$^{23}_D$: +10° (C=0.02, chloroform)

Mass (SI-MS): m/e 674 (M+H)+

Ultraviolet and Visible Range Absorption Spectrum: ($\lambda^{90\% \ methanol}_{max \ nm} E^{1\%}_{1 \ cm}$): 204 (277), 235 (609), 254 (352) 293 (114), 495 (217), 529 (143).

IR Spectrum ($\nu^{KBr}_{MAX} cm^{-1}$): 3400, 2930, 1600, 1435, 1405, 1295, 1240, 1195, 1165, 1090, 1070, 1010, 810, 775, 710

$^1$H-NMR Spectrum (CDCl$_3$, δppm): 1.12 (t, 3H), 1.21 (d, 3H), 1.30 (d, 3H), 2.1- (−, 2H), 2.20 (s, 6H), 3.63 (b, 1H), 3.76 (b, 1H), 4.1 (−, 2H), 4.55 (−, 1H), 4.91 (s, 1H), 5.02 (b, 1H), 5.16 (b, 1H), 5.50 (b, 1H), 7.33 (d, 1H), 7.72 (t, 1H), 7.90 (d, 1H).

EXAMPLE 4

270 mg of the crude converted extract obtained from the substrate Y262-3 in Example 1 was subjected to silicagel column chromatography in the same manner described in Example 2. Then the fraction comprising CG18B was proceeded in the same manner as in Example 2 for further purification by thin layer chromatography and acid-back dissolution. Thus 15 mg of a powder of CG18B was obtained.

Physico-chemical Properties of CG18B:

m.p. : 149° to 152° C. (decomposition)

[α]$^{23}_D$: −71° (C=0.02, chloroform)

Mass (SI-MS): m/e 658 (M+H)+

Ultraviolet and Visible Range Absorption Spectrum: ($\lambda^{90\% \ methanol}_{max \ nm} E^{1\%}_{1 \ cm}$): 204 (317), 231 (565), 258 (372) 290 (126), 436 (173).

IR Spectrum ($\nu^{KBr}_{MAX} cm^{-1}$): 3400, 2930, 1625, 1605, 1580, 1455, 1375, 1330, 1260, 1195, 1160, 1110, 1085, 1010, 810

$^1$H-NMR Spectrum [CDCl$_3$-CD$_3$OD (10:1), δppm]: 1.12 (t, 3H), 1.22 (d, 3H), 1.33 (d, 3H), 2,2- (−, 2H), 2.24 (s, 6H), 3.0 (−, 1H), 3.63 (b, 1H), 3.82 (b, 1H), 4.0 (−, 1H), 4.03 (q, 1H), 4.49 (q, 1H), 4.92 (b, 1H), 4.95 (−, 1H), 5.05 (b, 1H), 5.36 (b, 1H), 7.34 (dd, 1H), 7.72 (t, 1H), 7.82 (s, 1H), 7.89 (dd, 1H)

EXAMPLE 5

392 mg of the crude converted extract obtained from the substrate D788-5 in Example 1 was subjected to silicagel column chromatography (diameter 30 mm, Silicagel C-200, manufactured by Wako Pure Chemical Co., 40 g), whereupon the column content was developed with the solvents mentioned below in order to elute a partially purified fraction mainly comprising CG19A and a partial fraction mainly comprising CG19B.

1. Chloroform/methanol (20/1); 140 ml
2. Chloroform/methanol/water (100/10/0.1); 200 ml
3. Chloroform/methanol/water (70/10/0.1); 130 ml Then the fractions were processed in the same manner as in Example 2 for purification by thin layer chromatography and acid back-dissolution. Thus 27 mg of a pure powder of CG19A and 52 mg of a pure powder of CG19B were obtained.

Physico-chemical Properties of CG19A m.p. : 158° to 162° C. (decomposition)

[α]$^{23}_D$: +116° (C=0.02, chloroform)

Mass (SI-MS): m/e 686 (M+H)+

Ultraviolet and Visible Range Absorption Spectrum: ($\lambda^{90\% \ methanol}_{max \ nm} E^{1\%}_{1 \ cm}$): 204 (292), 234 (582), 252 (319) 289 (126), 479 (172), 494 (465).

IR Spectrum ($\nu^{KBr}_{MAX} cm^{-1}$): 3400, 2920, 1725, 1615, 1580, 1440, 1400, 1280, 1235, 1205, 1195, 1120, 1000, 825

$^1$H-NMR Spectrum (CDCl$_3$, δppm): 1.12 (t, 3H), 1.18 (d, 3H), 1.27 (b, 1H), 2.3 (b, 2H), 2.9–3.0 (m, 1H), 3.5 (b, 1H), 3.66 (b, 1H), 3.74 (s, 3H), 4.10 (s, 3H), 4.1–4.2 (−, 2H), 4.29 (s, 1H), 4.87 (b, 1H), 5.27 (b, 1H), 5.51 (b, 1H), 7.33 (d, 1H), 7.73 (t, 1H), 8.02 (d, 1H).

Physico-chemical Properties of CG19B m.p. : 200° to 204° C. (decomposition)

[α]$^{23}_D$: +49° (C=0.02, chloroform)

Mass (SI-MS): m/e 702 (M+H)+

Ultraviolet and Visible Range Absorption Spectrum: ($\lambda^{90\% \ methanol}_{max \ nm} E^{1\%}_{1 \ cm}$): 205 (292), 234 (591), 252 (324) 289 (124), 478 (175), 495 (169).

IR Spectrum ($\nu^{KBr}_{MAX} cm^{-1}$): 3400, 2925, 1725, 1615, 1580, 1440, 1400, 1280, 1235, 1205, 1195, 1155, 990, 805

$^1$H-NMR Spectrum (CDCl$_3$, δppm): 1.12 (t, 3H), 1.23 (d, 3H), 1.28 (d, 3H), 2.3 (b, 2H), 3.0 (m, 1H), 3.48 (b, 1H), 3.65 (b, 1H), 3.71 (s, 3H), 4.06 (s, 3H), 4.13 (—, 2H), 4.28 (s, 1H), 4.94 (b, 1H), 5.24 (b, 1H), 5.48 (b, 1H), 7.32 (d, 1H). 7.70 (t, 1H), 7.97 (d, 1H).

EXAMPLE 6

287 mg of the crude converted extract obtained from the substrate 13-dihydrocarminomycin in Example 1 was subjected to silicagel column chromatography (diameter 30 mm, Silicagel C-200, manufactured by Wako Pure Chemical Co., 25 g), whereupon the column content was developed with the solvents mentioned below in order to elute a partially purified fraction containing CG20A and a partially purified fraction containing CG20B.

1. Chloroform/methanol (20/1); 150 ml
2. Chloroform/methanol/water (100/10/0.1); 100 ml
3. Chloroform/methanol/water (70/10/0.1); 150 ml Then the fractions were processed in the same manner as in Example 2 for purification by thin layer chromatography and acid back-dissolution. Thus 35 mg of a pure powder of CG20A and 28 mg of a pure powder of CG20B were obtained.

Physico-chemical Properties of CG20A m.p. : 152° to 155° C. (decomposition)
$[α]^{23}_D$: +25° (C=0.02, chloroform)
Mass (SI-MS): m/e 630 (M+H)$^+$
Ultraviolet and Visible Range Absorption Spectrum ($λ^{90\% methanol}_{max\ nm}E^{1\%}_{1\ cm}$): 205 (263), 235 (544), 255 (429) 295 (116), 493 (228), 527 (157).
IR Spectrum ($ν^{KBr}_{MAX}cm^{-1}$): 3400, 2930, 1600, 1440, 1405, 1290, 1235, 1200, 1165, 1115, 1070, 1000, 820
$^1$H-NMR Spectrum [CDCl$_3$-CD$_3$OD (10:1), δppm]: 1.17 (d, 3H), 1.28 (d, 3H), 1.31 (d, 3H), 2.03 (b, H), 2.17 (b, 1H), 2.58 (d, 1H), 3.0-3.1 (m, 1H), 3.11 (d, 1H), 3.53 (b, 1H), 3.65 (—, 1H), 3.7 (—, 1H), 4.0-4.3 (—, 2H), 4.84 (b, 1H), 5.14 (b, 1H), 5.43 (b, 1H), 7.24 (dd, 1H), 7.66 (t, 1H), 7.78 (d, 1H).

Physico-chemical Properties of CG20B:

m.p. : 164° to 168° C. (decomposition)
$[α]^{23}_D$: −35° (C=0.02, chloroform)
Mass (SI-MS): m/e 646 (M+H)$^+$
Ultraviolet and Visible Range Absorption Spectrum ($λ^{90\% methanol}_{max\ nm}E^{1\%}_{1\ cm}$): 205 (263), 235 (539), 255 (425) 295 (116), 493 (225), 526 (155).
IR Spectrum ($ν^{KBr}_{MAX}cm^{-1}$): 3400, 2930, 1600, 1440, 1405, 1290, 1235, 1195, 1165, 1110, 1010, 990, 810
$^1$H-NMR Spectrum [CDCl$_3$-CD$_3$OD (5:1), δppm]: 1.25 (d, 3H), 1.28 (d, 3H), 1.31 (d, 3H), 1.8 -(—, 2H), 2.64 (d, 1H), 3.0 (m, 1H), 3.13 (d, 1H), 3.53 (b, 1H), 3.65 (b, 1H), 3.7 (—, 1H), 4.0-4.3 (—, 2H), 4.96 (b, 1H), 5.17 (b, 1H), 5.43 (b, 1H), 7.27 (d, 1H), 7.68 (t, 1H), 7.81 (d, 1H).

EXAMPLE 7

456 mg of the crude converted extract obtained from the substrate LB-1 in Example 1 was subjected to silicagel column chromatography (diameter 30 mm, Silicagel C-200, manufactured by Wako Pure Chemical Co., 38 g), whereupon the column content was developed with the solvents mentioned below in order to elute a partially purified fraction mainly comprising CG22A and a partially purified fraction mainly comprising CG22B.

1. Chloroform/methanol (20/1); 120 ml
2. Chloroform/methanol/water (100/10/0.1); 150 ml
3. Chloroform/methanol/water (70/10/0.1); 150 ml Then the fraction containing CG22A was processed in the same manner as in Example 2 for purification by thin layer chromatography and acid back-dissolution. Thus 38 mg of a pure powder containing CG22A was obtained. On the other hand, the fraction containing CG22B was concentrated to dryness and then purified by reversed phase silicagel chromatography as mentioned below.

Reversed Phase Silicagel Chromatography:
Column: diameter 23 mm (open)
Silicagel: UMC Gel (ODS) 60A, 170/120 mesh (manufactured by Yamamura Chemical Co.), 50 g
Solvent System: (1) Acetonitrile/0.05M ammonium formate (pH 4.0) (15/85) 450 ml (2) Acetonitrile/0.05M ammonium formate (pH 4.0) (20/80) 450 ml After development in order, a fraction containing CG22B was collected and adjusted to a pH of 8.0 with 1N sodium hydroxide. This was extracted with chloroform, washed with water and then concentrated to dryness. The resulting solid was dissolved in 1/50M acetic acid 9 ph 3.0) and washed by extracting twice with 15 ml of toluene. Then this was adjusted to a pH of 8.0 with 1N sodium hydroxide and extracted with 30 ml (total amount) of a mixed solvent of chloroform/methanol (10/1).

This was washed with water and dewatered (dried) with anhydrous sodium sulfate and thereafter concentrated. An excess amount of N-hexane was added thereto to form a precipitate, which was collected by filtration and dried in vacuum to obtain 15 mg of a pure powder of CG22B.

Physico-chemical Properties of CG22A m.p. : 163° to 165° C. (decomposition)
$[α]^{23}_D$: +51° (C=0.02, chloroform)
Mass (SI-MS): m/e 644 (M+H)$^+$
Ultraviolet and Visible Range Absorption Spectrum: ($λ^{90\% methanol}_{max\ nm}E^{1\%}_{1\ cm}$): 206 (254), 235 (651), 254 (373) 293 (123), 495 (239), 529 (156).
IR Spectrum ($ν^{KBr}_{MAX}cm^{-1}$): 3400, 2930, 1600, 1440, 1405, 1295, 1240, 1200, 1170, 1120, 1070, 1020, 1000, 775.
$^1$H-NMR Spectrum [CDCl$_3$-CO$_3$OD (5:1), δppm]: 1.10 (t, 3H), 1.17 (d, 3H), 1.30 (d, 3H), 2.18 (—, 2H), 2.35 (s, 3H), 2.5-2.8 (m, 1H), 3.63 (b, 1H), 3.76 (b, 1H), 3.8-4.2 (—, 2H), 4.85 (s, 1H), 4.85 (—, 1H), 5.12 (b, 1H), 5.47 (b, 1H), 7.32 (d, 1H), 7.71 (t, 1H), 7.85 (dd, 1H).

Physico-chemical Properties of CG22B m.p. : 167° to 172° C. (decomposition)
$[α]^{23}_D$: +49° (C=0.02, chloroform)
Mass (SI-MS): m/e 660 (M+H)$^+$
Ultraviolet and Visible Range Absorption Spectrum: ($λ^{90\% methanol}_{max\ nm}E^{1\%}_{1\ cm}$): 206 (255), 235 (653), 255 (373) 293 (122), 495 (240), 529 (157).
IR Spectrum ($ν^{KBr}_{MAX}cm^{-1}$): 3400, 2940, 1600, 1440, 1405, 1295, 1240, 1200, 1170, 1120, 1070, 1015, 990, 810, 775.
$^1$H-NMR Spectrum [CDCl$_3$-CO$_3$OD (5:1), δppm]: 1.11 (t, 3H), 1.27 (d, 3H), 1.33 (d, 3H), 2.18 (—, 2H), 2.37 (s, 3H), 2.6-2.8 (m, 1H), 3.64 (bd, 1H), 3.77 (b, 1H), 3.9-4.3 (—, 2H), 4.87 (s, 1H), 4.98 (b, 1H), 5.13 (b, 1H), 5.47 (b, 1H), 7.31 (dd, 1H), 7.72 (t, 1H), 7.88 (dd, 1H).

EXAMPLE 8

From a slant agar culture of Streptomyces galilaeus KE303 (FERM BP-2048), a loopful of the microbial cells was taken out. This was inoculated in 100 ml of a sterilized seed culture medium (comprising the components mentioned below) which was put in a 500 ml Erlenmeyer flask and then cultivated on a rotary shaker at 28° C. for 48 hours with shaking to prepare a seed culture.

| Seed Culture Medium: | |
|---|---|
| Soluble Starch | 1.5% |
| Glucose | 1.0 |
| Soybean Powder | 1.0 |
| Yeast Extract | 0.3 |
| Sodium Chloride | 0.3 |
| Dipotassium Phosphate | 0.1 |
| Magnesium Sulfate (7H$_2$O) | 0.1 |
| Copper Sulfate (5H$_2$O) | 0.0007 |
| Iron Sulfate (7H$_2$O) | 0.0008 |
| Zinc Sulfate (7H$_2$O) | 0.0002 |
| Tap water | |
| pH 7.4 (before sterilized) | |

Next, 50 ml of a fermentation and production medium comprising the same composition as the seed culture medium except that the soybean powder was increased to 2% and the yeast extract was increased to 0.2% was put in each of 400 Erlenmeyer flasks of 500 ml capacity and sterilized. 1 ml of the above-mentioned seed culture was inoculated in each production medium flask and incubated on a rotary shaker (210 rpm) at 28° C. for 24 hours with shaking. A methanol solution of D788-7 (2.5 mg/ml) was added to each flask in an amount of 1 ml/flask (final concentration: 50 μg/ml), and then the incubation was continued for a further 41 hours.

The culture broth was recovered (about 38 liters in all) and subjected to centrifugation to separate the mycelial cells. Then the mycelial cake was extracted with 10 liters of acetone to obtain a converted product. The acetone extract was concentrated under reduced pressure to about ⅓ volume and then adjusted to a pH of 8.0 with 4N sodium hydroxide. Then the product was back-dissolved in 4 liters (total amount) of chloroform, dried with anhydrous sodium sulfate, filtered and concentrated under reduced pressure. An excess amount of isopropyl ether was added thereto to form a precipitate, which was collected by filtration, washed with ethyl ether and dried to obtain 682 mg of a crude powder of the converted product.

EXAMPLE 9

All the crude converted product powder obtained in Example 8 was dissolved in chloroform and then subjected to silicagel column chromatography formed by suspension in chloroform (diameter 34 mm, Wako Gel C-200, manufactured by Wako Pure Chemical Co.), whereupon the column content was developed with the solvents mentioned below in order to elute fractions each in an amount of 20 g.

1. Chloroform/methanol (20/1); 400 ml
2. Chloroform/methanol 930.1); 300 ml
3. Chloroform/methanol/water (200/10/0.1); 400 ml
4. Chloroform/methanol/water (100/10/0.1); 400 ml
5. Chloroform/methanol/water (80/10/0.1); 500 ml
6. Chloroform/methanol/water (60/10/0.1); 500 ml Each fraction was checked by the use of a silicagel plate 60, F$_{254}$ (manufactured by Merck Co.) with a developing solvent of chloroform/methanol/water (50/10/0.1), whereby a fraction of the converted product CG15A and that of the converted product CG15B were pooled. The same amount of water was added to each of the thus pooled fractions and the pH value was adjusted to be 8.0. After being shaken, the chloroform layer separated was taken out and concentrated to dryness under reduced pressure to obtain a partially purified product of CG15A and a partially purified product of CG15B.

Next, each of these products was dissolved in a small amount of a mixed solvent of chloroform/methanol (30/1) and the resulting solution was crosswise spotted on 10 sheets of fractionating thin silicagel plate (60 PF$_{254}$ manufactured by Merck Co.) at a position 1.5 cm above the bottom end thereof. These were then developed with a mixed solvent of chloroform/methanol/water (50/10/0.1) for the CG15A-containing fraction and with a mixed solvent of chloroform/methanol/water (50/12/0.1) for the CG15B-containing fraction. The reddish violet band corresponding to each main component was scraped and collected and then extracted with a mixed solvent of chloroform/methanol (2/1). The resulting extract was concentrated to dryness under reduced pressure and then dissolved in a small amount of a mixed solvent of chloroform/methanol (1/2). The resulting solution was passed through a gel filtration column (Φ1.1 cm × 14 cm; Toyopearl HW-40, manufactured by Toso Soda Co., 10 ml) as formed with the same solvent system, whereupon the column content was developed with the same solvent system to obtain a purified fraction.

The thus obtained pure fraction was concentrated to dryness and then dissolved in 30 ml of 1% acetic acid. The resulting solution was extracted twice with toluene and washed. The aqueous layer was further washed with 30 ml ethyl ether, adjusted to a pH of 8.0 with an aqueous saturated solution of sodium bicarbonate solution and then extracted with chloroform (30 ml, two times). The chloroform extract layer was washed with an aqueous saturated solution of sodium chloride and then concentrated to dryness to obtain a pure powder of CG15A (80.2 mg) and a pure powder of CG15B (68.5 mg).

The physico-chemical properties of CG15A and those of CG15B obtained as above are as follows.

CG15A

1. Shape: Violet Powder
2. m.p. : 209°–214° C.
3. Molecular Weight: 635 (M+H)$^+$(SI mass)
4. UV and Visible Range Absorption Spectrum

| Solvent | $\lambda_{max}$ (E$^{1\%}_{1\ cm}$) |
|---|---|
| 90% methanol | 203 (298), 235 (651) |
|  | 254 (382), 293 (123) |
|  | 495 (236), 527 (162) |
|  | 592 (42) |
| 0.01 N HCl | 204 (290), 235 (678) |
| 90% methanol | 255 (385), 293 (127) |
|  | 495 (246), 529 (158) |
| 0.01 N NaOH | 206 (205), 241 (673) |
| 90% methanol | 296 (119), 562 (233) |
|  | 597 (176) |

5. IR Spectrum: ($\nu_{MAX}$cm$^{-1}$) (KBr) 3400, 2930, 1590, 1430, 1300, 1240, 1200, 1170, 1120, 1070, 1000

6. $^1$H-NMR Spectrum: δppm: in CDCl$_3$-CD$_3$OD (10:1) 1.09 (t, 3H), 1.19 (d, 3H), 1.30 (d, 3H), 1.7–2.0 (m, 8H), 2.0–2.2 (—, 2H), 3.00 (m, 1H), 3.54 (b, 1H), 3.68 (b, 1H), 4.19 (bq, 2H), 4.79 (s, 1H), 4.88 (b, 1H), 5.04 (b, 1H), 5.41 (b, 1H), 7.22 (d, 1H), 7.62 (t, 1H), 7.68 (d, 1H)

CG15B

1. Shape: Violet Powder
2. m.p.: 192°–196° C.
3. Molecular Weight: 646 (M+H)+ (SI mass)
4. UV and Visible Range Absorption Spectrum

| Solvent | $\lambda_{max}$ (E$^{1\%}_{1\,cm}$) |
|---|---|
| 90% methanol | 204 (300), 235 (585) |
| | 254 (347), 293 (99) |
| | 495 (207), 529 (142) |
| | 588 (20) |
| 0.01 N HCl | 204 (293), 235 (597) |
| 90% methanol | 255 (348), 293 (101) |
| | 495 (219), 529 (138) |
| 0.01 N NaOH | 207 (675), 241 (589) |
| 90% methanol | 295 (99), 563 (208) |
| | 599 (161) |

5. IR Spectrum: ($\nu_{MAX}$cm$^{-1}$) (KBr) 3400, 2920, 1600, 1430, 1290, 1235, 1195, 1165, 1110, 1005, 980
6. $^1$H-NMR Spectrum: δppm: in CDCl$_3$-CD$_3$OD (10:1) 1.11 (t, 3H), 1.26 (d, 3H), 1.27 (d, 3H), 1.7–2.0 (m, 6H), 2.0–2.3 (—, 2H), 2.9–3.2 (m, 1H), 3.51 (b, 1H), 3.67 (b, 1H), 4.0–4.3 (m, 3H), 4.86 (s, 1H), 4.97 (b, 1H), 5.11 (b, 1H), 5.45 (b, 1H), 7.3 (d, 1H), 7.71 (t, 1H), 7.86 (d, 1H)

While the invention has been described in detail and with reference to specific embodiments thereof, it will be apparent to one skilled in the art that various changes and modifications can be made therein without departing from the spirit and scope thereof.

What is claimed is:

1. Anthracycline antibiotics of a formula (I):

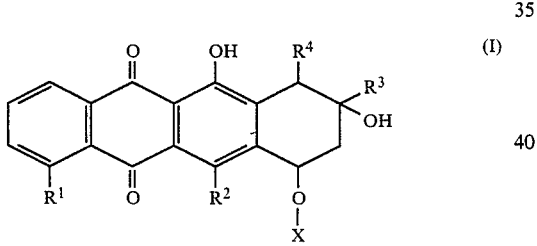

in which R$^1$ and R$^2$ are hydroxyl groups, R$^3$ is ethyl group, R$^4$ is methoxycarbonyl group and X represents daunosamine-rhodenose or daunosamine-dexyfucose; or R$^1$ and R$^2$ are hydroxyl groups, R$^3$ is 1-hydroxyethyl group, R$^4$ is hydrogen atom and X represents daunosamine-rhodenose or daunosamine-deoxyfucose; or R$^1$, R$^2$ and R$^4$ are hydroxyl groups, R$^3$ is ethyl group and X represents daunosamine-rhodenose, daunosamine-deoxyfucose, rhodosamine-rhodenose, N-monomethyldaunosamine-rhodenose or N-monomethyldaunosamine-deoxyfucose; or R$^1$ is methoxy group, R$^2$ is hydroxyl group, R$^3$ is ethyl group, R$^4$ is methoxycarbonyl group and X represents daunosamine-rhodenose or daunosamine-deoxyfucose; or R$^1$ and R$^4$ are hydroxy groups, R$^2$ is hydrogen atom, R$^3$ is ethyl group and X represents daunosamine-deoxyfucose, as well as pharmaceutically acceptable acid addition salts thereof.

2. An anthracycline antibiotic as claimed in claim 1, which is CG17A of a formula:

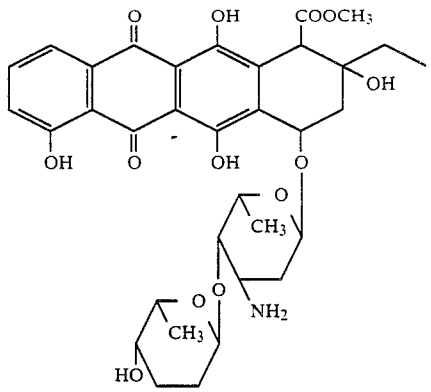

3. An anthracycline antibiotic as claimed in claim 1, which is CG17B of a formula:

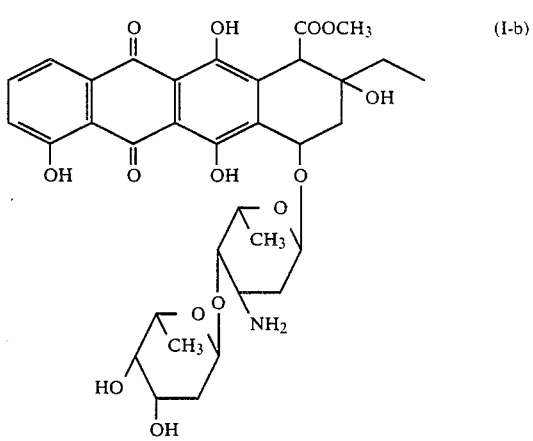

4. An anthracycline antibiotic as claimed in claim 1, which is CG19A of a formula:

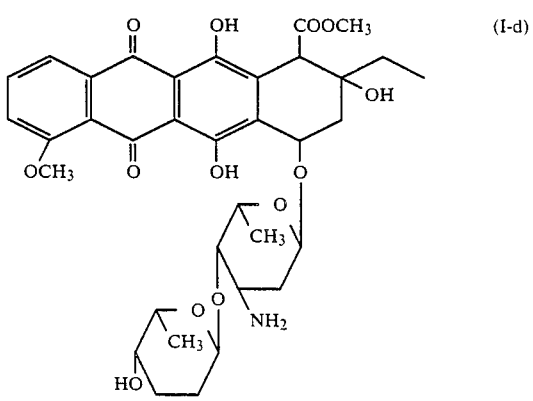

5. An anthracycline antibiotic as claimed in claim 1, which is CG19B of a formula:

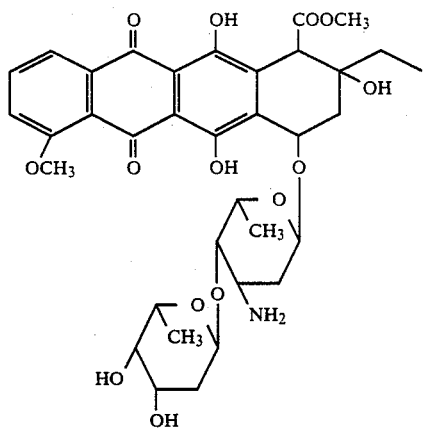

6. An anthracycline antibiotic as claimed in claim 1, which is CG20A of a formula:

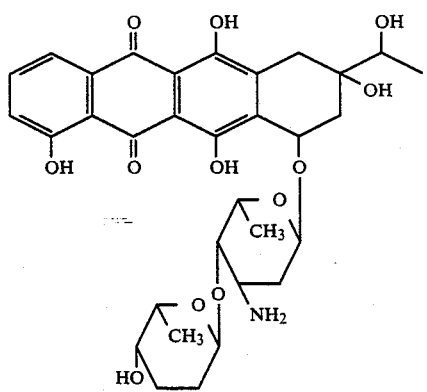

7. An anthracycline antibiotic as claimed in claim 1, which is CG20B of a formula:

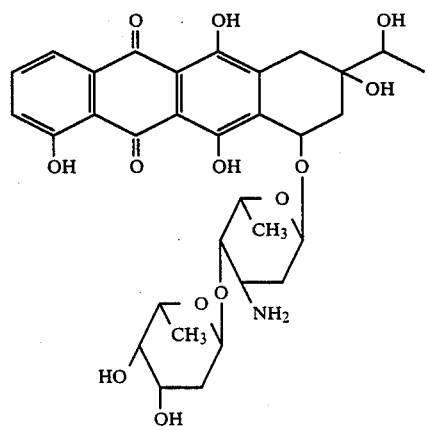

8. An anthracycline antibiotic as claimed in claim 1, which is CG22A of a formula:

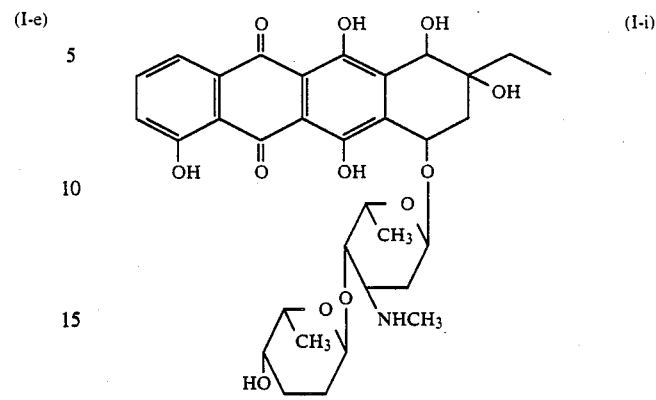

9. An anthracycline antibiotic as claimed in claim 1, which is CG22B of a formula:

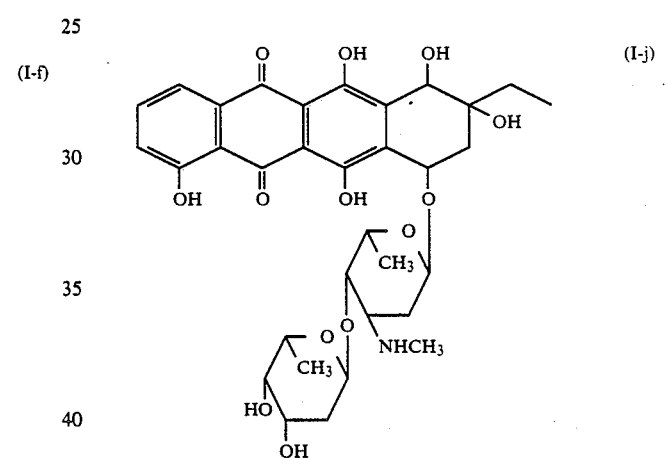

10. An anthracycline antibiotic as claimed in claim 1, which is CG15A of a formula:

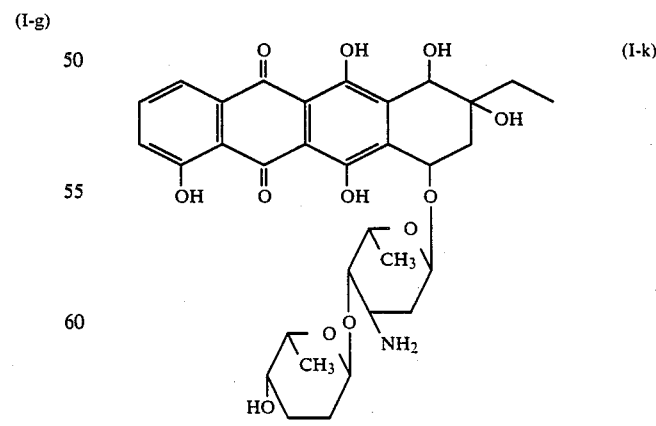

11. An anthracycline antibiotic as claimed in claim 1, which is CG15B of a formula:

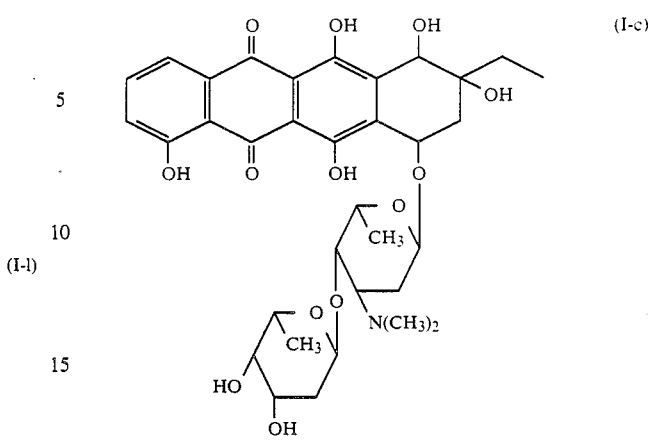
13. An anthracycline antibiotic as claimed in claim 1, which is CG21A of a formula:
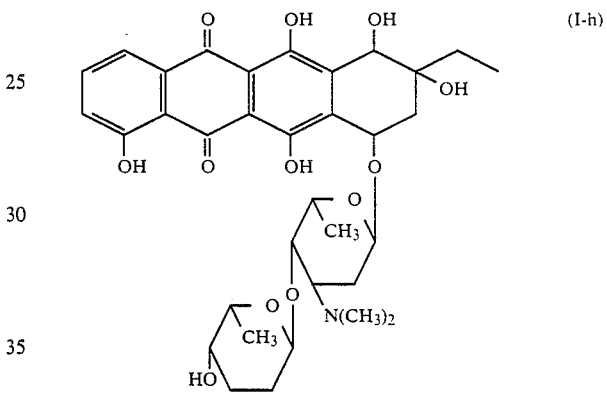
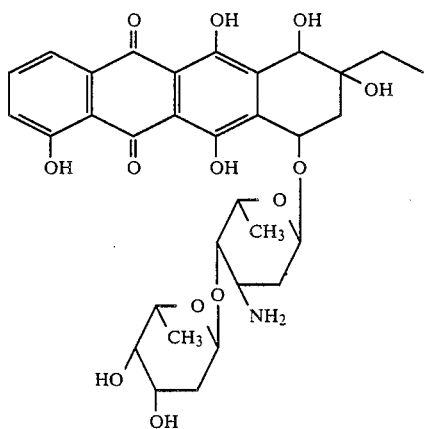
12. An anthracycline antibiotic as claimed in claim 1, which is CG18B of a formula:
* * * * *